(12) United States Patent
Morgenbrod et al.

(10) Patent No.: US 9,115,862 B2
(45) Date of Patent: Aug. 25, 2015

(54) COLOUR-TUNABLE LIGHT SOURCE UNIT WITH PHOSPHOR ELEMENT

(75) Inventors: Nico Morgenbrod, Berlin (DE); Henning Rehn, Berlin (DE)

(73) Assignee: OSRAM GmbH, Munich (DE)

( * ) Notice: Subject to any disclaimer, the term of this patent is extended or adjusted under 35 U.S.C. 154(b) by 223 days.

(21) Appl. No.: 13/818,390

(22) PCT Filed: Aug. 24, 2010

(86) PCT No.: PCT/EP2010/062310
§ 371 (c)(1),
(2), (4) Date: Feb. 22, 2013

(87) PCT Pub. No.: WO2012/025141
PCT Pub. Date: Mar. 1, 2012

(65) Prior Publication Data
US 2013/0155648 A1    Jun. 20, 2013

(51) Int. Cl.
| F21V 9/00 | (2006.01) |
| A61B 1/06 | (2006.01) |
| G02B 27/09 | (2006.01) |
| G02B 19/00 | (2006.01) |
| F21V 13/02 | (2006.01) |
| G02B 5/00 | (2006.01) |
| F21V 8/00 | (2006.01) |
| G02B 15/14 | (2006.01) |
| G02B 23/24 | (2006.01) |

(52) U.S. Cl.
CPC ............... *F21V 9/00* (2013.01); *A61B 1/0638* (2013.01); *A61B 1/0653* (2013.01); *A61B 1/0669* (2013.01); *F21V 13/02* (2013.01); *G02B 19/0028* (2013.01); *G02B 19/0047* (2013.01); *G02B 27/0944* (2013.01); *G02B 27/0955* (2013.01); *G02B 5/001* (2013.01); *G02B 6/0008* (2013.01); *G02B 15/14* (2013.01); *G02B 23/2469* (2013.01)

(58) Field of Classification Search
None
See application file for complete search history.

(56) References Cited

U.S. PATENT DOCUMENTS

| 2007/0103927 A1 | 5/2007 | Guo et al. |
| 2010/0231863 A1 * | 9/2010 | Hikmet et al. ............... 353/31 |
| 2011/0248624 A1 * | 10/2011 | Kishimoto et al. ......... 313/483 |

FOREIGN PATENT DOCUMENTS

| DE | 102007037875 A1 | 2/2009 |
| TW | 200719070 A | 5/2007 |

(Continued)

OTHER PUBLICATIONS

English language abstract for DE 10 2007 037 875 A1 dated Feb. 12, 2009.

(Continued)

*Primary Examiner* — Britt D Hanley

(57) ABSTRACT

The invention concerns a light source unit of tunable spectral properties, having a pump light source and a phosphor element for a conversion of pump light into converted light intended for illuminating a target, wherein the phosphor element has at least two phosphor element sections interacting differently with pump light, and wherein the light source unit further comprises a deflecting unit, such as a zoom lens or a variable diffraction grating, for deflecting the pump light so as to vary a distribution of pump light incident onto the phosphor element with respect to the different phosphor element sections, in order to vary spectral properties of the combined converted light beam emanating from the light source unit.

20 Claims, 15 Drawing Sheets

(56) References Cited

FOREIGN PATENT DOCUMENTS

| TW | 200732699 A | 9/2007 |
| WO | 2009021859 A1 | 2/2009 |
| WO | 2009047683 A2 | 4/2009 |
| WO | 2009147582 A1 | 12/2009 |

OTHER PUBLICATIONS

Taiwanese Office Action for Application No. 100129897; Jan. 22, 2014; 12 pages (with translation).

* cited by examiner

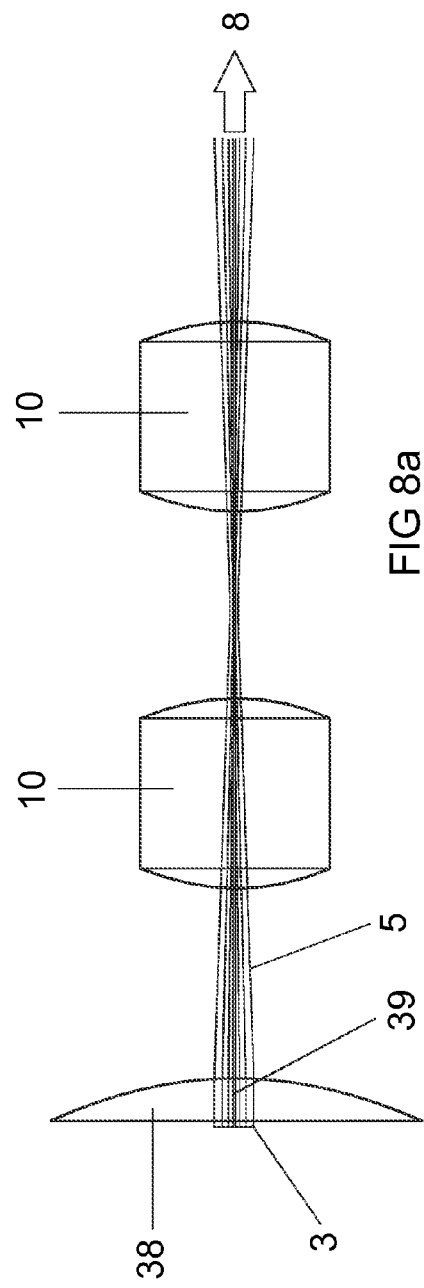
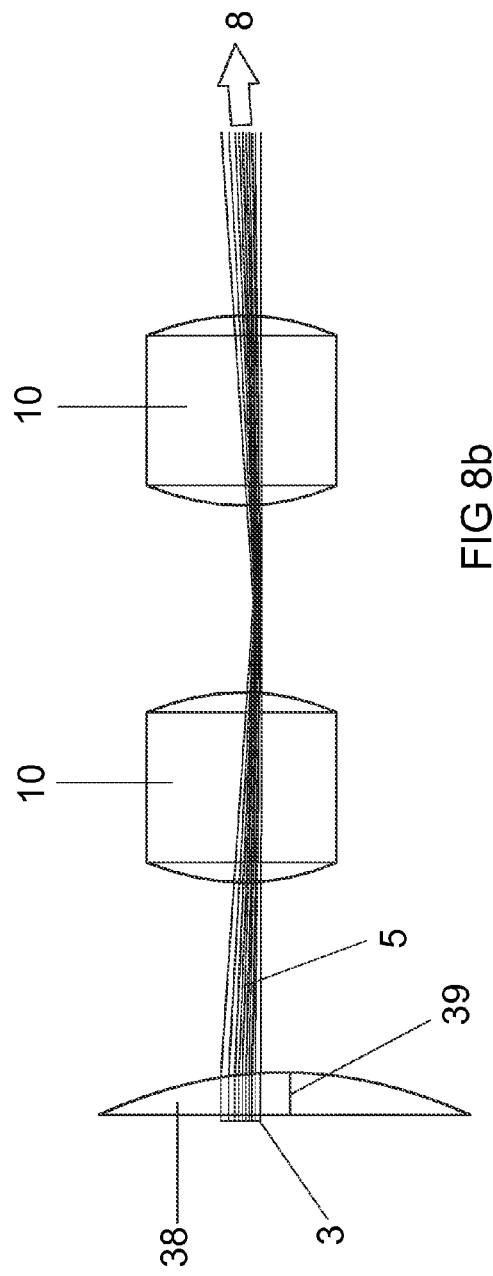
FIG 8a
FIG 8b

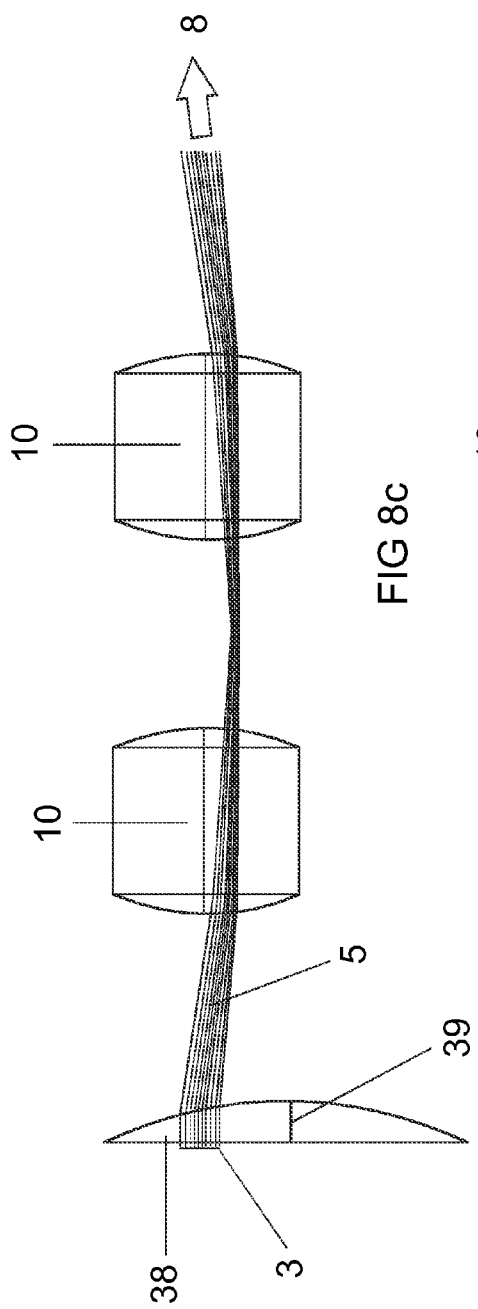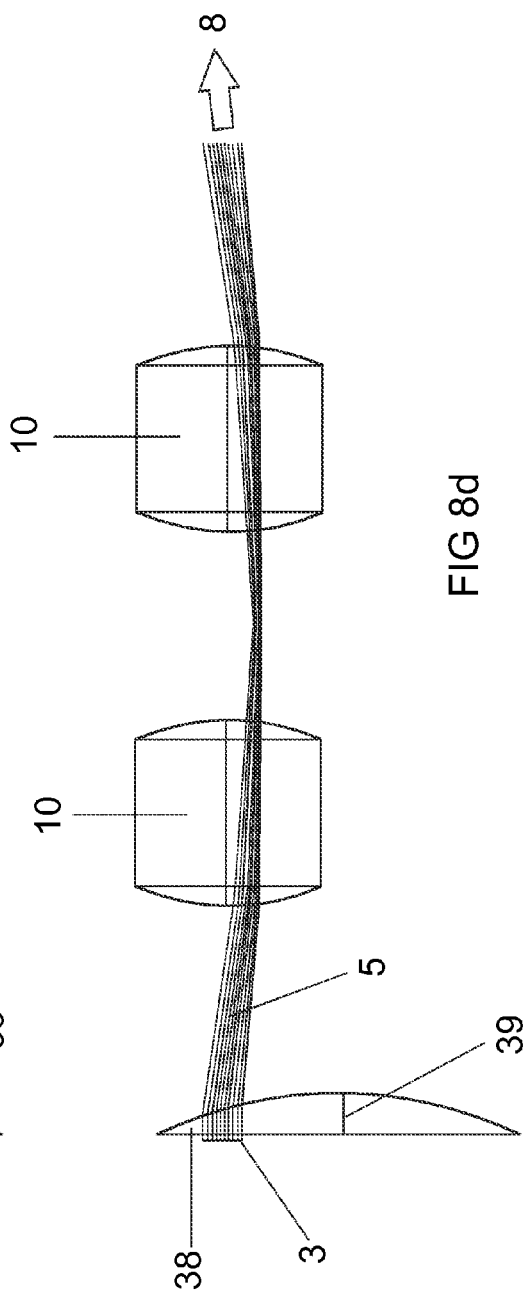

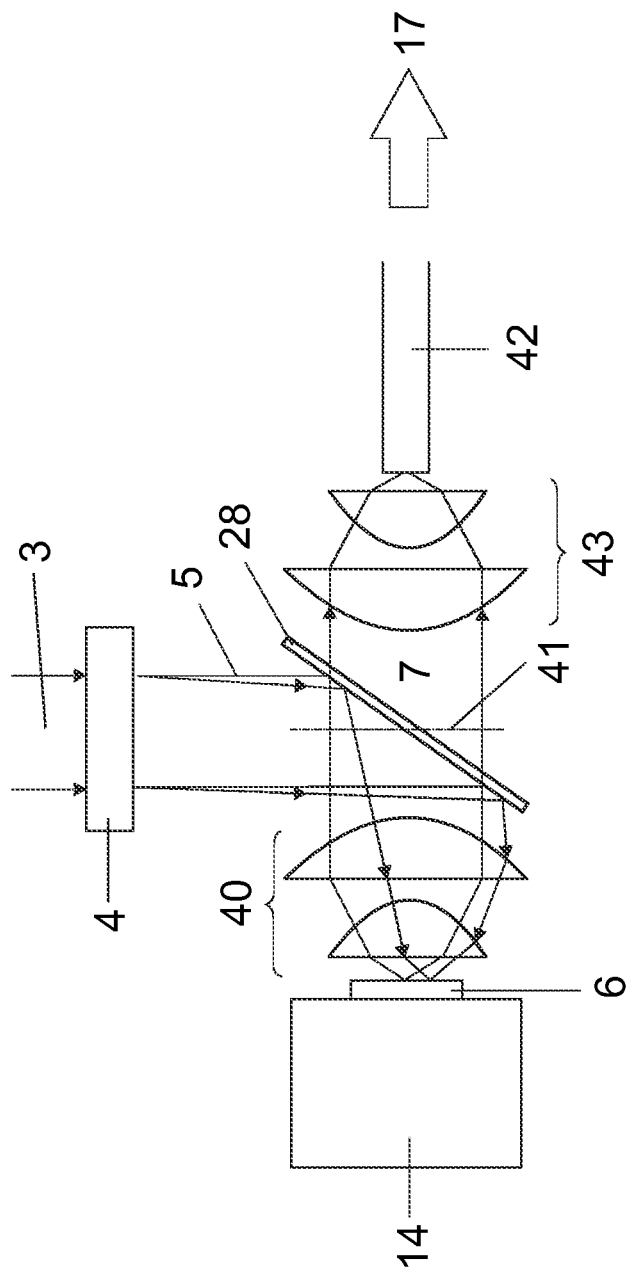

COLOUR-TUNABLE LIGHT SOURCE UNIT WITH PHOSPHOR ELEMENT

RELATED APPLICATIONS

The present application is a national stage entry according to 35 U.S.C. §371 of PCT application No.: PCT/EP2010/062310 filed on Aug. 24, 2010.

FIELD OF THE INVENTION

The invention relates to a light source unit comprising a pump light source for an emission of pump light and a phosphor element for a conversion of said pump light into converted light for further use.

BACKGROUND OF THE INVENTION

There is an increasing need for high luminance colour-tunable light sources, in particular tunable white light sources, but also tunable ultraviolet and infrared light sources, in applications from illumination systems for surgical operating fields, spotlight and data projection systems to a fibre-optical illumination in medical and industrial endoscopy. Concerning white light of high luminance, bright discharge lamps are the state of the art being broadly used today. Recent developments are heading for a combination of solid-state light sources, in particular light emitting diodes (LED) and light converting phosphor elements. Therein, the typically blue or ultraviolet solid-state based light is converted to light having a longer wavelength by a transmission through the phosphor element.

In prior art, a high luminance solid state white light source is obtained for example by arranging a big number of white and colour LEDs in a two-dimensional array, wherein the output colour of such an LED aggregate is tuned by switching on and off the individual colour LEDs.

SUMMARY

Various embodiments of the present disclosure, alternately referred to herein as 'the invention' are disclosed, wherein the phosphor element comprises at least two phosphor element sections interacting differently with the pump light and being suitably arranged for being irradiated in at least one of a simultaneous and a selective manner by the pump light, and wherein the light source unit further comprises a deflecting unit for deflecting at least a part of the pump light for varying the irradiation of the phosphor element by altering a distribution of the pump light incident onto it with respect to the different phosphor element sections in order to vary spectral properties of the converted light.

The invention is further directed to a method for varying spectral properties of light emanating from a light source unit according to the invention, the method comprising a step of adjusting the deflecting unit for altering a distribution of the pump light incident on the phosphor element with respect to the phosphor element sections.

The invention is furthermore directed to a corresponding use of a light source unit according to the invention for a surgical illumination system for illuminating a surgical operating field, for a moving head spotlight, a data projection system or a fibre-optical illumination system.

Preferred embodiments of the invention are specified in the dependent claims and, in addition, appear from the following description. Therein, the details refer to all aspects of the invention and are thus meant as being disclosed individually.

Further, no distinction will be made in detail between process, use and apparatus features of the invention, so that the following disclosure is to be comprehended with respect to all those categories.

The present disclosure describes using a phosphor element having at least two different phosphor element sections yielding converted light with respectively different spectral properties when irradiated by pump light. By altering relative pump light portions incident on the different phosphor element sections, respectively, the spectral composition of the combined converted light beam emanating from the combined phosphor element can thus be tuned.

Preferably, the combined phosphor element is a single but compound element. Further, the phosphor element sections are preferably arranged side by side in one plane.

In a simple case, the phosphor element contains only two different phosphor element sections, which are arranged adjacently and are made of a different phosphor material each. Irradiating such a phosphor element by a single pump light source, one can vary the relative portions of the pump light incident on the respective phosphor element sections by deflecting the pump light beam, for instance, using a scanning mirror. As a result, the spectral content of the combined converted light beam is variable and controllable in an easy manner without a necessity of manipulating the pump light source or of using an additional light source.

However, employment of two or more different pump light sources emitting pump light of respectively different wavelengths is also conceivable in a light source unit according to the invention. This can e.g. be advantageous if different phosphor materials employed exhibit a maximal effectivity of conversion for pump light of significantly different wavelengths.

As is already recognizable from the simple example employing a scanning mirror, a deflecting unit according to the invention can be implemented so as to allow also a continuous variation of spectral properties of the combined converted light, besides the discrete variation known from systems according to the prior art mentioned above, if this is desired for the intended application.

A phosphor material constituting an individual phosphor element section may be a single phosphor type or a combination of phosphor types, each of which converts the pump light by an absorption of the pump light and an emission of a converted light having a longer wavelength, wherein a spontaneous emission, not a stimulated emission, is dominant. Phosphor types illustrating, though not limiting the present invention are Ce or Eu doped YAG (Yttrium Aluminum Garnet) or Eu doped strontium orthosilicate.

In the context of the present invention, no strict restriction of the pump light or the converted light to a certain range of the electromagnetic spectrum needs to be done. Neither is the use of the terms "irradiation" and "illumination" meant to be restricting in this sense.

Nevertheless, for typical applications intended, the range reaching from the infrared to the ultraviolet light will be suited. Preferably, the converted light will lie in the visible light range, the pump light being ultraviolet and/or visible light.

In a particularly preferred embodiment of a phosphor element according to the invention, the individual phosphor element sections are rotationally symmetric in an incidence plane of the pump light with respect to a main propagation direction of the pump light. Throughout the present disclosure, a main propagation direction of a light beam is understood as a mean or an averaged direction of propagation, e.g. in case of a diverging or a converging beam.

As a counterpart to the rotational symmetry, an adjacent arrangement of, for instance, rectangular phosphor element sections is also conceivable. An obvious advantage of rotationally symmetric phosphor element sections lies in the rotational symmetry of a major part of conventional optical elements, such as lenses, needed to manipulate the incident pump light and the emitted converted light.

In a preferred embodiment of a light source unit according to the invention, the deflecting unit is designed as a variable diffraction grating for decomposing the initial pump light beam into partial pump light beams deflected according to different diffraction orders. The partial pump light beams exit the grating at a respective diffraction angle each, the corresponding angular distribution being dependent on the grating structure. Here, the variation of the angular distribution of the deflected pump light can, for example, be performed by mechanically exchanging the grating in a revolver.

Alternatively, a diffraction grating having a variable grating structure can be implemented as an acousto-optical modulator (AOM), wherein a phase grating is generated in form of standing waves excited piezo-electrically, or as a device generating visual structures, such as DLP (Digital Light Processing), LCD (Liquid Crystal Display), LCOS (Liquid Crystal on Silicon), wherein the pump light is diffracted at represented structures In a phase grating, operating in transmission, multiple grating periods can be superimposed yielding additional possibilities to vary the diffraction angle distribution of the pump light exiting the phase grating. In general, the process of generating a specific phase grating to be irradiated by the pump light in order to obtain a desired angular distribution for the deflected pump light beam is similar to a process of generating a hologram and irradiating the same by a reference light beam.

In another preferred embodiment, the deflecting unit comprises a lens system, the term lens system referring to a single lens or a system of more than one lenses throughout the whole of the present disclosure, for example designed as a zooming optical system. Therein, a zooming lens is moved longitudinally in the beam of pump light intended for incidence on the phosphor element in order to vary its angular extent and/or its cross-sectional extent. The irradiation of the phosphor element by a pump light beam of a varying angular extent results in irradiating an area of a varying size on the surface of the phosphor element.

In an advantageous variant of this embodiment, the lens system comprises a cone shaped lens, a so-called axicon lens, shaping an annular profile in a beam of pump light initially having a circular profile shape and being incident on the axicon lens along its axis. Again, besides imposing a ring-shaped profile to the initial pump light beam, a continuous zoom function can be obtained in such an axicon lens system comprising more than one lens by longitudinally moving one of the lenses in the beam relatively to the other lenses. In particular, a combination of more than one axicon lenses is conceivable in this context.

As an alternative to a moving of a lens along the pump light beam, a deflecting lens system is also possible wherein a lens is moved transversally to the pump light beam for varying the angle of deflection of the deflected pump light.

In a particularly preferred embodiment of a light source unit according to the invention, the pump light beam having a desired angular distribution, with respect to the initial direction of its propagation, imposed to it by the deflecting unit, is coupled to a light guide for being transmitted to a remote phosphor element. Here, on the one hand, the light guide performs a transmitting function to bridge a spatial separation between the pump light source and the deflecting unit on the one side and the phosphor element on the other side.

In particular, this enables a flexible spatial arrangement of the phosphor element with respect to the pump light source and the deflecting unit, which can thus be adapted to an intended application without imposing restrictions on the spatial configuration and the size of the pump light source, its cooling system, and the deflecting unit. As a consequence, a high power pump light source, such as a laser source, can be employed here to achieve a correspondingly high luminance for the converted light beam.

On the other hand, rotationally symmetrical light guides are also known to generate a rotationally symmetric light distribution with respect to the light guide axis in a light beam coupled to them. Naturally, this function of a light guide becomes particularly important in a light source unit according to the invention in cases where the pump light beam exiting the deflecting unit lacks rotational symmetry in direction space, whereas the phosphor element to be irradiated by the pump light is rotationally symmetric.

As a light guide, a glass fibre is suited as well as a particularly flexible fibre filled with a liquid, but also a hollow waveguide having reflecting inner walls; the choice depends on the intended application.

Preferably, a coupling lens system is provided between an exit face of the deflecting unit and an entry face of the light guide for coupling the deflected pump light to the light guide by providing an image of the exit face of the deflecting unit at the entry face of the light guide. The coupling lens system is capable of coupling the deflected pump light, which, according to the invention, has a variable angular distribution, to the light guide without a necessity of adapting the relative positions of the entry face of the light guide and the exit face of the deflecting unit as that angular distribution is varied.

Alternatively, the entry face of the light guide can be positioned in contact with or close to the exit face of the deflecting unit.

In some applications, it is further reasonable to provide a focusing lens system between an exit face of the light guide and the phosphor element for transmitting the pump light exiting the light guide towards the phosphor element. This is in particular important in arrangements where the lateral extent of the pump light beam incident on the phosphor element would otherwise exceed the size of the surface of incidence of the phosphor element.

In most cases, such a lens or lens system will be focusing the distinct partial pump light beams propagating at an individual deflection angle imposed by the deflecting unit each, to the intended phosphor element section, respectively. Furthermore, if the phosphor element is operated in a reflection mode described in more detail further below, the focusing lens can simultaneously be used for collimating the converted light emanating from the phosphor element.

In fact, for applications requiring a collimated converted light beam, as for example in a spotlight device, a collecting lens system can be provided for collecting and collimating at least a part of the converted light emanating from the phosphor element.

Preferably, the collecting lens system is suitably designed and arranged with respect to the phosphor element so as to provide a plane where converted light that is emitted by the phosphor in one direction is focused. An aperture stop in this plane is then the exit pupil of the lens or lens system and for the beam of the converted light.

Accordingly, the light emitted from a position on the phosphor plane completely fills the exit pupil but propagates in one direction. This exit pupil is particularly suited for mixing the above-mentioned fractions of the combined converted light beam, emanating from the different phosphor element sections, the mixing function being treated in more detail further below.

Alternatively, in a particularly favourable embodiment of a light source unit according to the invention, the exit pupil of the collecting lens system is used to position a mirror therein, for directing the pump light to the phosphor element when the latter is operated in reflection. Typically, the normal vector of the mirror surface will enclose an angle of 45° with both the main direction of propagation of the converted light and the main direction of propagation of the pump light incident on the mirror.

Further, if a conventional mirror is used, reflecting both the pump light and the converted light, a projection of the mirror onto the cross section of the converted light beam shall be small compared to the area of this cross section. In such a case, a placing of the mirror in the exit pupil of the collecting lens system is particularly advantageous, as any shadowing of the combined converted light beam in the exit pupil does not cut any specific part from it but, instead, homogeneously reduces its brightness.

By preference, the coupling of pump light to the phosphor element which is operated in reflection is realized by a dichroic mirror, which for example reflects the pump light and transmits the converted light at an incidence angle of 45°. The performance of a dichroic mirror, which can for example be an interference mirror having a layer system, will typically depend on the incidence angle of the light.

In a particularly preferred embodiment of the light source unit, a mixing optical element is provided in a path of the combined converted light for mixing the respective fractions of the converted light beam emanating from the different phosphor element sections, the mixing being performed across the cross-sectional area of the combined converted light beam. Since these fractions of the converted light beam emanating from the different phosphor element sections in general possess slightly different main propagation directions relative to each other, the respective areas illuminated on a possibly remote target may be shifted with respect to each other, this shifting being the bigger the longer the distance of a free-field propagation of the converted light towards the target is.

Indeed, in case a collecting lens system is provided, a nearly homogenous mixture of the fractions of the converted light beam emanating from the different phosphor element sections in a desired proportion is obtained in its exit pupil. It is, in general, not maintained over a long distance of propagation for the above-mentioned reasons though. For applications including a free-field propagation of the combined converted light over a considerable distance, as for instance in the case of spotlight or data projection systems, a mixing optical element is preferably provided to prepare a combined converted light beam having a uniform cross-sectional distribution of spectral properties at the target.

The mixing optical element can, for example, be implemented as a fly's eye condenser, which comprises two two-dimensional arrays of lenses or micro lenses arranged perpendicularly to the main propagation direction of the converted light beam, or as an additional positive or negative lens or lens system which forms an image of a point of the exit pupil of the collecting lens or lens system to the far field or on a distant target.

In any case, the position and the configuration of the mixing optical element is adjusted so as to obtain perfectly overlapping cross-sectional areas of the respective fractions of the converted light beam emanating from the different phosphor element sections, having a homogenous intensity distribution each, at a target which is to be illuminated.

As already mentioned above, the mixing optical element is preferably arranged in the exit pupil of a collecting lens system, if present, where the cross sections belonging to the different fractions of the converted light beam emanating from the different phosphor element sections nearly overlap and the mixing thus needs to be performed only with respect to the respective propagation directions of the respective fractions of the converted light beam.

Preferably, a main direction of propagation of the pump light incident on the phosphor element and a main direction of propagation of the converted light at the phosphor element are approximately opposite to each other. In other words, the phosphor element is preferably operated in a reflection mode, wherein a deviation of +/−45° from 180° is also considered as "opposite direction". This operation mode has an advantage that at least a part of optical elements, in particular lenses, employed to prepare the incident pump light beam can be simultaneously used for preparing the converted light beam for further use. This is, for example, the case in the above-mentioned embodiment where a focusing lens for the pump light simultaneously functions as a collecting lens for the converted light. This leads, among other advantages depending on the intended application, to a reduction of the space required for the light source unit as a whole.

In a preferred embodiment employing the reflection operation mode, the phosphor element is provided on a heat sink not being translucent for the pump light. The heat sink transfers heat generated inside the phosphor element for example due to the Stokes shift during the conversion process, away from the phosphor element. Therefore, a material having a good thermal conductivity is preferably used for the heat sink, for example a metal, such as copper, aluminium or alloys thereof. Further, the heat sink is preferred to have a large surface for transmitting heat to a surrounding medium, for example to surrounding air, so that also cooling fins can be provided.

As a counterpart of the reflection operation mode, an operation of the phosphor element in transmission can also be preferred, for instance, for applications which do not require additional optical elements to be provided in the beam of the converted light. This can become important, for instance, in a special case of an endoscopic application, where a phosphor element can be arranged in the vicinity of the distal end of a light guide and facing the target to be illuminated by the converted light.

In the transmission operation mode, usually a main direction of propagation of the pump light incident on the phosphor element and a main direction of propagation of the converted light at the phosphor element approximately coincide. In analogy to the reflection operation mode, a deviation of +/−45° from 0° is also considered as "coinciding directions".

In this mode, preferably, a dichroic mirror transmitting the pump light and reflecting the converted light, those properties being provided for normal incidence in either case, is backing the phosphor element or is provided in a path of the incident pump light for reflecting at least a part of the converted light emitted by the phosphor element in a direction opposite to either of the main propagation directions, the so-called backscattered photons.

In the following, the invention is exemplified by means of embodiments, wherein the features disclosed therein can be significant for the invention also in other combinations and implicitly relate, as mentioned above, to all categories of the invention.

BRIEF DESCRIPTION OF THE DRAWINGS

FIGS. 8A-8D show a laterally shifted and thus deflecting lens as an example for a deflecting unit according to the invention.

FIG. 11 shows an embodiment of a light source unit suited for an application in a fibre-optical illumination system.

DETAILED DESCRIPTION

Figure 1:
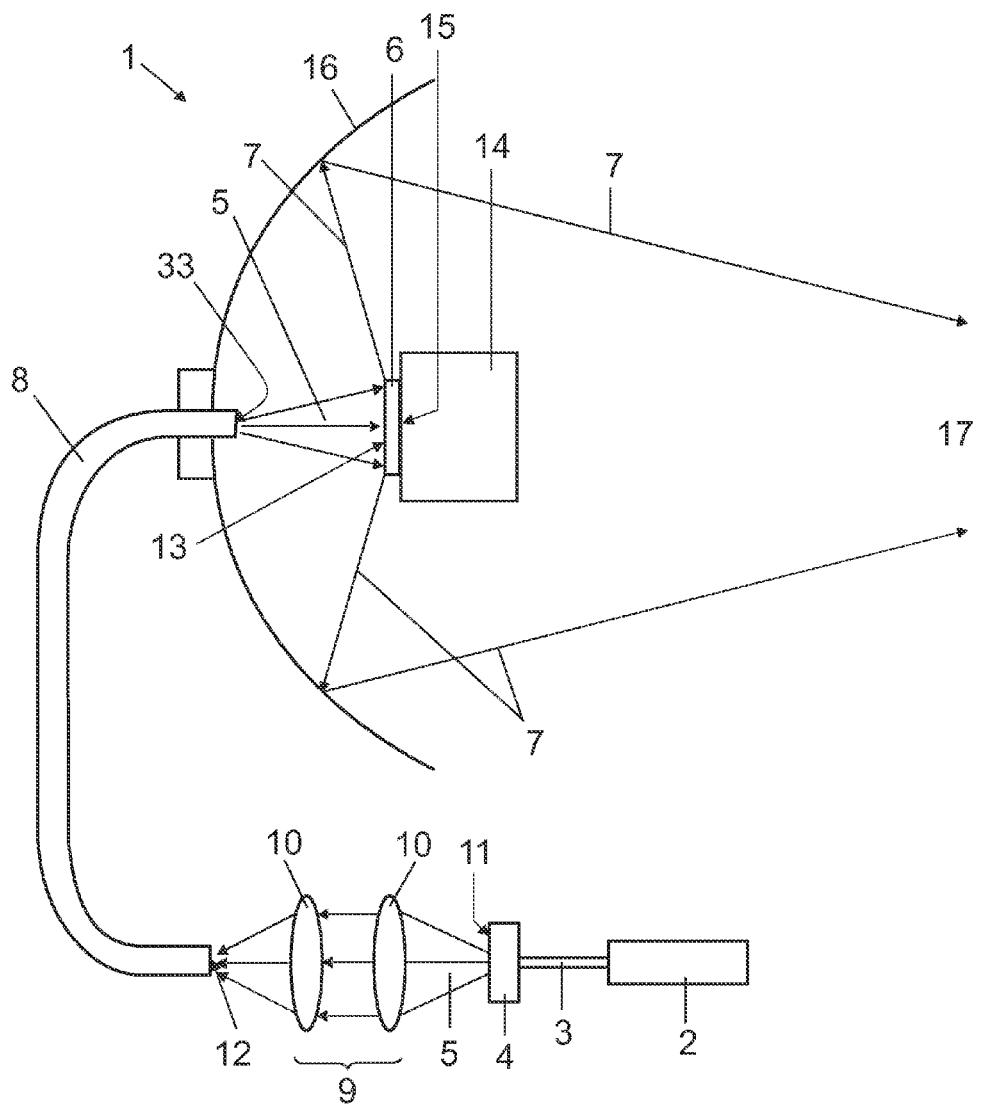
FIG. 1 illustrates an embodiment of a light source unit suited for an application for illuminating a surgical operating field.

FIG. 1 schematically displays an embodiment of a light source unit according to the invention, which is suited for an application in a surgical illumination system for illuminating a surgical operating field. A laser light source 2 emanates pump light with a wavelength typically lying in the ultraviolet range or in a short-wavelength part of the visible range. An initial pump light beam 3 enters a deflecting unit 4 which generates a deflected pump light beam 5 intended for irradiating a remote phosphor element 6. The deflected pump light beam 5 possesses a specific angular distribution, imposed by the deflecting unit 4, corresponding to a desired spectral composition of a converted light 7 emanated by the phosphor element 6 upon irradiation with the deflected pump light 5.

Figure 3:
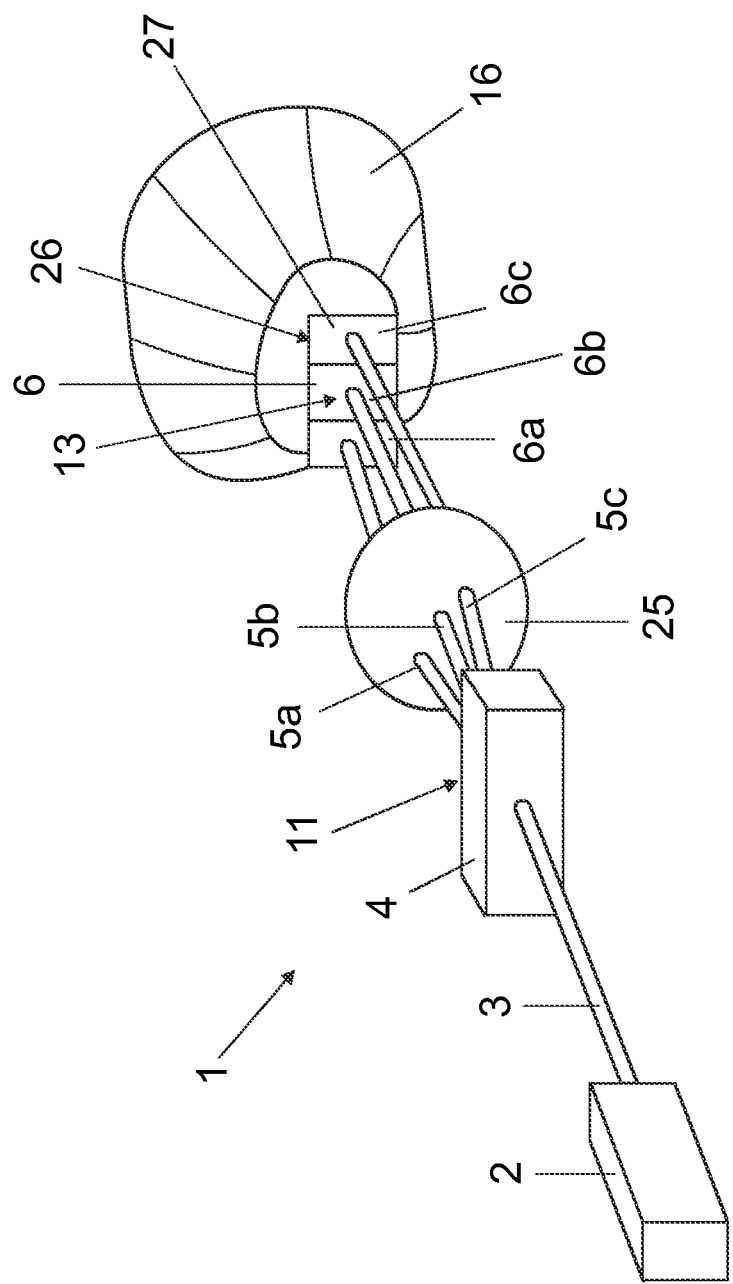
FIG. 3 shows an embodiment of a light source unit wherein the phosphor element sections have a rectangular shape.

According to the invention, the phosphor element 6 is a combined phosphor element comprising at least two phosphor element sections, as shown in FIGS. 3, 4 further below, which interact with the pump light 5 in a different manner. An individual phosphor element section may consist of a single phosphor type or of a phosphor material being a mixture of two or more different phosphor types, as specified above and in more detail further below, converting pump light into converted light of lower energy, typically lying in the visible range.

The deflected pump light 5 is transmitted to the remote phosphor element 6 by a light guide 8 designed so as to retain both the intensity and the polar angular distribution of the deflected pump light 5 over a distance of its transmission, possible implementations of the light guide being specified further above. Further, a coupling lens system 9 represented by two positive lenses 10 is provided between an exit face 11 of the deflecting unit 4 and an entry face 12 of the light guide 8 for coupling the deflected pump light 5 to the light guide 8 by forming an image of the exit face 11 on the light guide entry face 12.

In FIG. 1, the phosphor element 6 is operated in a reflection mode, i.e. the deflected pump light 5 is incident onto the same face surface 13 of the phosphor element 6 from which the converted light 7 intended for further use emanates. As an advantage of such a configuration, a cooling element 14 is provided at the back side 15 of the phosphor element 6 for cooling it during the conversion process. The surface 15 shall be reflecting for both the pump light and the converted light in order to achieve a maximum output for the light source unit 1.

Finally, a reflector 16 is provided for collimating the converted light 7 and for directing it to a target 17 to be illuminated by the converted light, which may be a surgical operating field in this example.

An optimal size of the phosphor element 6 can be obtained applying etendue conservation. Etendue is the product of source area and the projected solid angle of the source's output, multiplied by the square of the refractive index of the optical medium surrounding the source, which can be taken to be nearly 1 for air here. The optimum size of the phosphor disc is then chosen by making its etendue equal to the etendue of the application. Assuming the phosphor element 6 to be a diffuse Lambertian emitter into a hemisphere, having a circular shape in the incidence plane 13, a typical etendue value of 2200 $mm^2sr$ defined by target area, target distance and the diameter of the main reflector, would lead to an optimal radius equal to 15 mm for the phosphor element 6.

Figure 2:
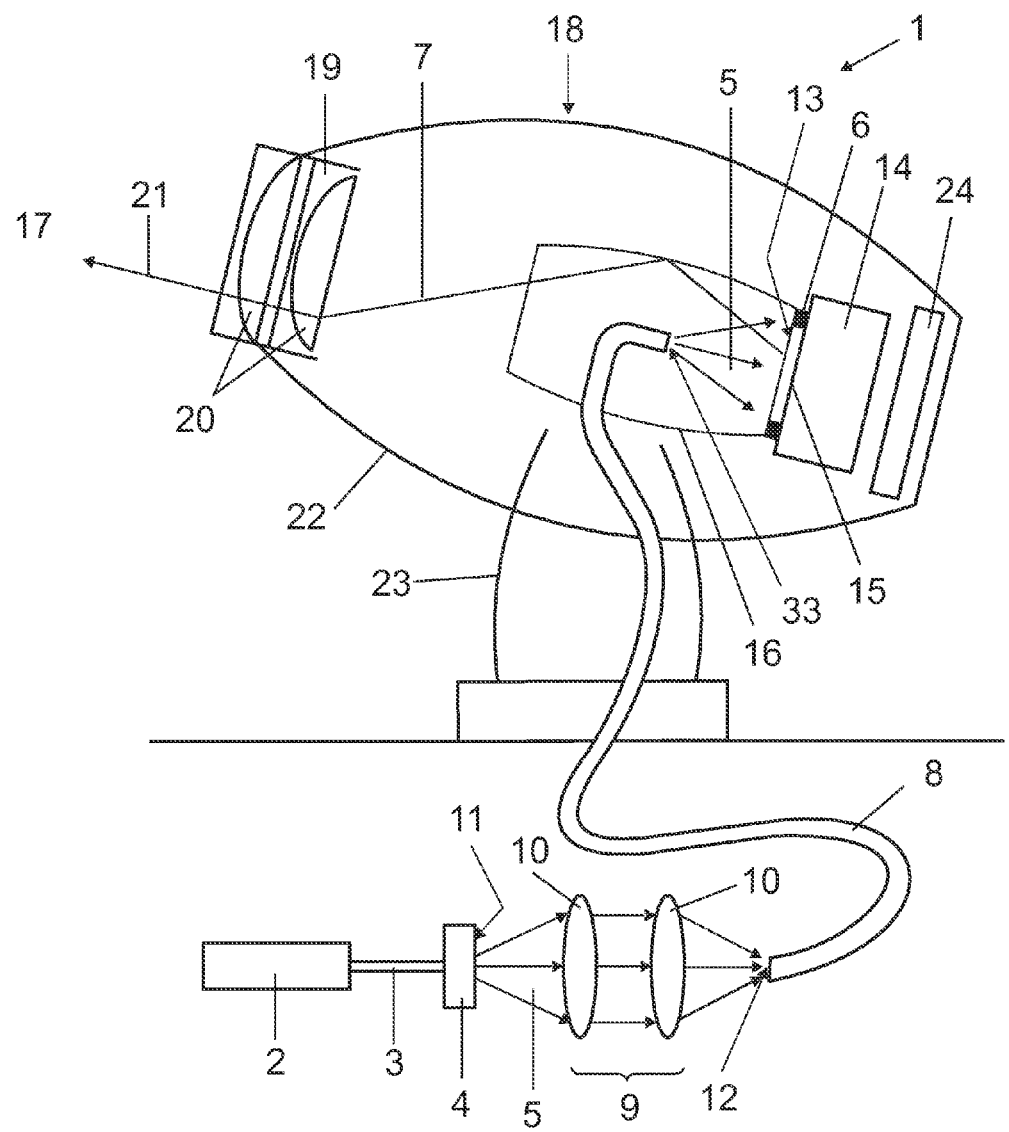
FIG. 2 shows an embodiment of a light source unit in an application in a moving head spotlight.

In FIG. 2, a slightly modified embodiment of a light source unit 1 according to the invention is displayed, which is suited for an application in a moving head spotlight device. Throughout the figures of the present disclosure, similar elements of the light source unit 1 will be denoted by identical reference signs. Here again, the pump light laser source 2, the deflecting unit 4, the coupling lens system 9 and the entry face 12 of the light guide 8 are situated in a stationary and stable manner remotely from the actual application device, here the moving head spotlight 18. In particular, there is no restriction concerning a size, a weight, and a position of the deflecting unit 4 or a cooling system for the laser 2.

According to the invention, the deflection of the initial pump light beam 3 by the deflecting unit 4 is variable so as to obtain a desired angular distribution in the deflected pump light beam 5, with respect to the direction of propagation of the initial pump light beam 3. In the present example, this is accomplished by means of a variable diffraction grating, with possible implementations being specified above.

For the purpose of illuminating a target 17 located at a large distance from the phosphor element 6, the converted light beam 7 primarily collimated by the reflector 16 is further processed by a projecting optical system 19, in particular comprising positive lenses 20. The resulting converted light beam 21 is a collimated light beam, with the colour being adjusted by choosing an appropriate setting of the deflecting unit 4. The beam 21 has fixed direction of propagation with respect to the projecting optical system 19, whereas a directing towards the target is eventually performed by moving the housing 22 of the moving head spotlight 18 with respect to its stationary base 23.

In this embodiment, the light guide 8 receives an additional function of providing a mechanically flexible connection between the pump light source 2 and the deflecting unit 4 on the one side and the phosphor element 6 with the collimating optic 16 and 19 on the other side, besides the function of transmitting the deflected pump light 5. Thus, a particularly flexible fibre filled with a liquid medium translucent for the pump light is employed.

Finally, a fan 24 is provided at the back side of the cooling element 14 for intensifying the heat exchange of the phosphor element 6 and of the whole device 18 with the environment.

Analogously to FIG. 1, an optimal radius of the phosphor element 6 as a source of converted light 7, 21, having a circular shape in the incidence plane 13, can be determined from a typical value of 750 mm$^2$sr for the etendue of this device to be equal to 9 mm.

In FIG. 3, a further embodiment of a light source unit 1 according to the invention is illustrated, which is for example suited for an application in a simple stationary spotlight for illuminating a stage or a studio with light of a variable colour. Here, the phosphor element 6 operated in transmission consists of three rectangular phosphor element sections 6a, 6b, and 6c arranged adjacently in a plane 13 of incidence of pump light 5.

The initial pump light beam 3 is decomposed by the deflecting unit 4, which is a diffraction grating as described above, into partial deflected pump light beams 5a, 5b, and 5c corresponding to different diffraction orders, respectively. A focusing lens 25 is provided between the exit face 11 of the deflecting unit 4 and the phosphor element 6 for directing the deflected pump light beams 5a/5b/5c to the incidence surface 13 of the phosphor element 6.

By altering the settings of the diffraction grating constituting the deflecting unit 4, the intensity of the initial pump light beam 3 can be redistributed between the partial deflected pump light beams 5a/5b/5c while the respective deflection angles are varied as well. As a result, the irradiance of the pump light incident on the individual phosphor element sections 6a/6b/6c is varied. Converted light emanating from the opposite face side 26 of the phosphor element 6 is then collimated by the reflector 16 and thereby directed towards a target (not shown).

By preference, a dichroic mirror 27 transmitting pump light and reflecting converted light is provided at the front face 13, which is a back side of the phosphor element 6 as viewed from the target, for reflecting the backscattered converted light photons. In order to collect a major part of the converted light by the reflector 16, the dichroic mirror 27 shall preferably completely cover the back side 13 of the phosphor element 6 here.

In FIG. 4, a top view of a phosphor element 6 according to the invention having rotationally symmetric phosphor element sections 6a/6b/6c/6d with respect to a direction of pump light propagation is displayed for exemplary combinations a), b), and c) of phosphor materials.

In the case of a rotational symmetry of the phosphor element 6, it can be used for conversion of pump light in a most effective way compared to other geometries. This is due to the fact that a pump light beam having a rotationally symmetric angular distribution can be prepared and modified employing conventional optical elements, such as rotationally symmetric lenses or light guides. In contrast thereto, it appears difficult to prepare a pump light beam perfectly matching the geometry of a rectangular phosphor element 6 as displayed in FIG. 3, for example. In addition, a rotationally symmetric phosphor element enables a simpler and more efficient optical design for rotationally symmetric targets as in the case of surgical lamps or spot lights.

Phosphor element sections 6a-6d, as shown in FIG. 4, can, for instance, be fabricated using hollow coaxial glass or metal cylinders as substrates whose front faces are coated by a respective phosphor element each, for example employing an electrophoretic method. As concerns the thickness of a phosphor element 6, a full conversion of the incident pump light to converted light is typically obtained for ¼ mm to ½ mm thick phosphor element slices. When working in a reflection operation mode, it can also be taken into account that the phosphor element 6 is then passed by a pump light beam twice.

Figure 4A:
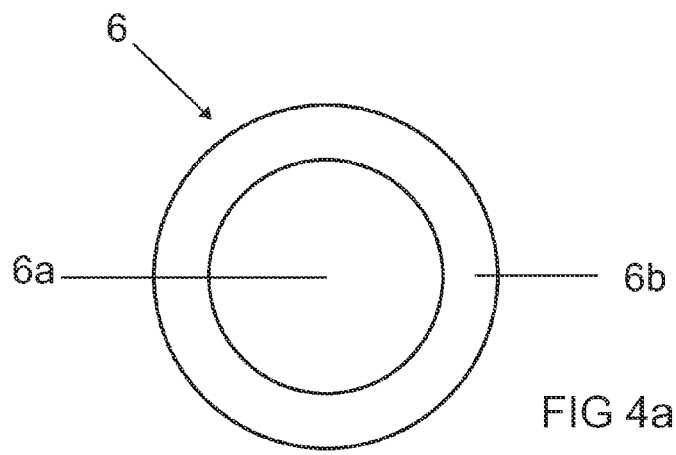
FIGS. 4A-4C show a top view of exemplary phosphor elements according to the invention having annular phosphor element sections.

In FIG. 4a), the phosphor element section 6a is designed to emit converted light of a so-called mint white colour, the corresponding phosphor material known to be particularly effective concerning the output of the conversion process. The displayed combination with a phosphor element section 6b designed to emit converted light in the red spectral range yields an efficient warm white light source by superimposing the converted light beams emitted by the individual phosphor element sections 6a/6b, respectively.

Regarding the relative areas of the respective phosphor element sections 6a/6b, the different phosphor materials are combined to an equal area subject to irradiation by the pump light in the present example. However, preferably a different effectivity of the respective conversion processes for different phosphor types or phosphor materials is also taken into account in the design of the respective sections of the combined phosphor element, as for instance shown in the following FIGS. 4b), 4c).

Figure 4B:
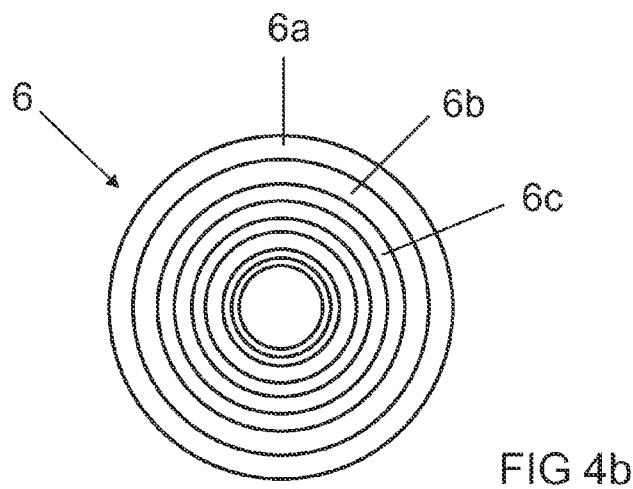

In FIG. 4b), a combination of three different phosphor types designed to emit converted light in the red, green, and blue spectral range, respectively, exemplarily represented by phosphor element sections 6a/6b/6c, allows to obtain an arbitrary colour in the superimposed converted light beam by choosing a suited distribution of the pump light intensity over the displayed surface of the phosphor element 6. In particular, a combination of more than one different pump light sources, as for example more than one laser sources emitting pump light in differing spectral ranges being particularly efficient for distinct phosphor materials used, respectively, is also conceivable in cases like this.

Figure 4C:
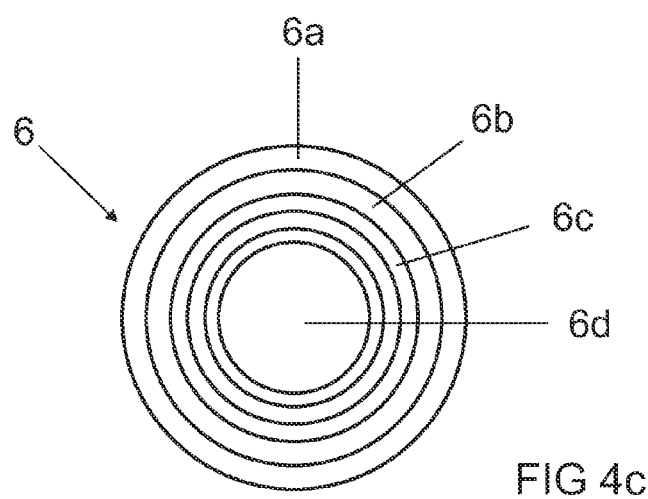

In FIG. 4c), a combination of phosphor types designed for emitting a red, green, and blue converted light, exemplarily represented by the sections 6a/6b/6c, with a phosphor material designed for an emission of a white converted light, constituting the central phosphor element section 6d, is displayed.

Figure 5A:
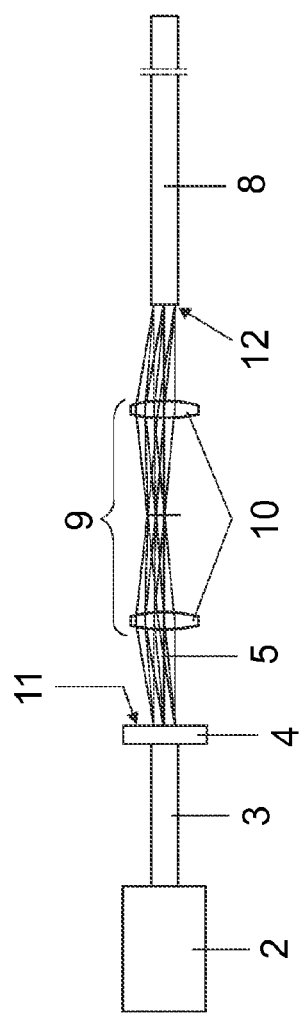
FIG. 5A shows a part of a light source unit according to the invention, wherein the deflected pump light is coupled by a coupling lens system to a light guide to be transmitted to the phosphor element.

In FIG. 5a), a coupling of the deflected pump light beam 5 to the light guide 8 corresponding to the schematic illustration in FIGS. 1 and 2 is shown in more detail. Therein, the imaging optical system 9 is represented by two identical positive lenses 10 arranged symmetrically and imaging the exit face 11 of the deflecting unit 4 to the entry face 12 of the light guide 8 with a magnification value equal to 1 in this exemplary case.

In the present embodiment, the light guide 8 can fulfil a double function. Besides transmitting the deflected pump light 5 to a remote phosphor element 6, the light guide 8 having a rotational symmetry with respect to the light guide axis further imposes the rotational symmetry with respect to this axis to the transmitted pump light beam 5, preserving the polar angular distribution imposed to it by the deflecting unit 4. The described function of the light guide 8 is, for instance, important in embodiments where the deflection unit 4 is designed as a diffraction grating whose grating structure lacks a radial symmetry in the plane of its exit face 11.

Figure 5B:
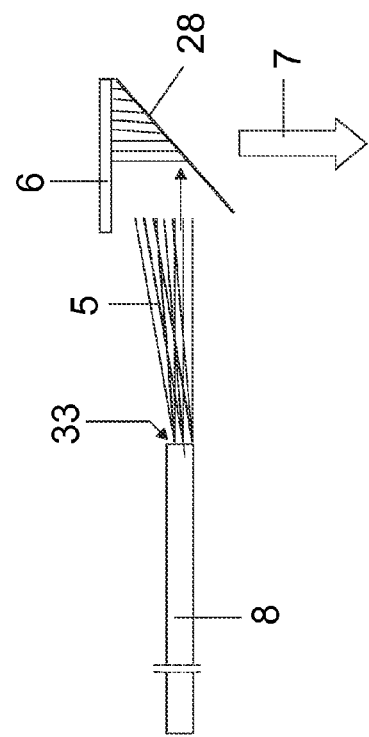
FIG. 5B shows a part of a light source unit according to the invention, wherein a mirror reflects the light from an exit face of the light guide onto the phosphor element.

In FIG. 5b), the deflected pump light beam 5 exiting the light guide 8 propagates to a dichroic mirror 28 which is designed to reflect the pump light and to transmit the converted light 7 at an incidence angle of 45°. Thus, the beam 5 is directed to the phosphor element 6, which is operated in a reflection mode. For the sake of clarity, one half of the rotationally symmetric beam 5 has been omitted in this figure.

Figure 6A:
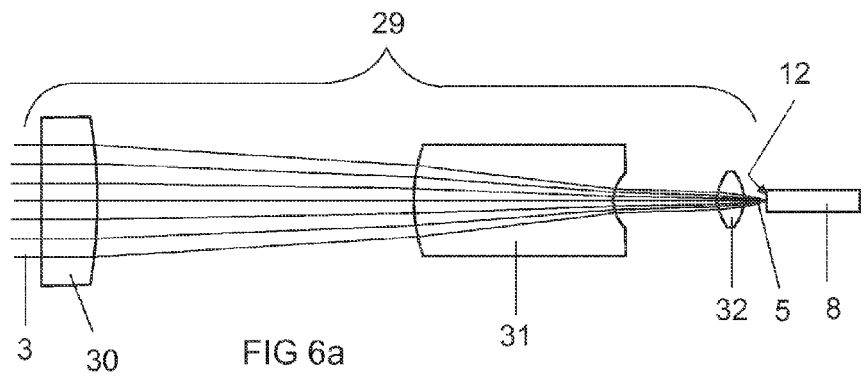
FIGS. 6A-6C show a zoom lens system as an example for a deflecting unit according to the invention.
Figure 6B:
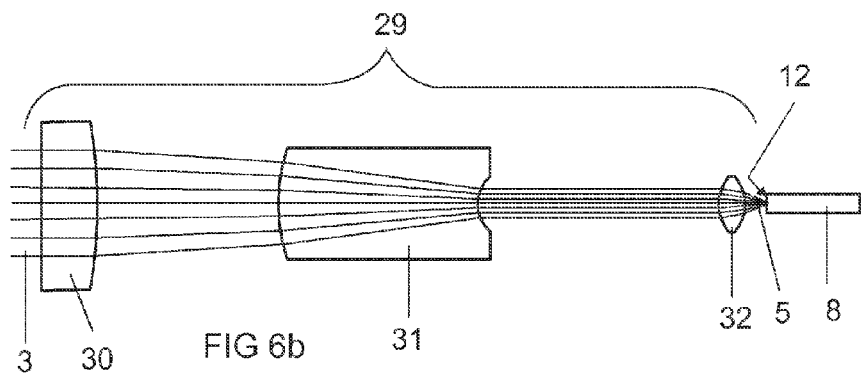
Figure 6C:
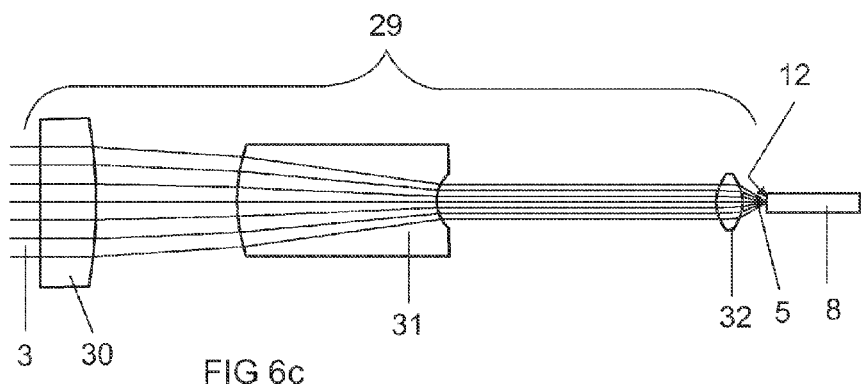

In FIG. 6, the deflecting unit according to the invention is implemented as a zoom lens system 29, here comprising three lenses 30, 31, and 32. In this embodiment, the angular distribution of the initial pump light beam 3 is varied by moving the central zoom lens 31 along the pump light beam with respect to the stationary lenses 30 and 32. Preferably, the initial pump light beam 3 has already been expanded before entering the deflecting unit 29. For different positions of the central zoom lens 31, exemplarily represented in FIGS. 6a)-6c), the angular extent of this deflected pump light beam 5 entering the light guide 8 is altered from 10° in FIGS. 6a) to 40° in FIG. 6c).

Transmitting the deflected pump light beam 5 prepared as illustrated in FIG. 6, by the light guide 8 to a remote phosphor element 6 for instance, in a manner displayed in FIGS. 1 and 2, a circular area on the incidence surface 13 of the phosphor element 6 will be homogeneously irradiated by the pump light beam 5, wherein the size of the irradiated area is defined by the angular extent of the beam 5 as well as by the distance between the exit face 33 of the light guide 8 (cf. FIGS. 1 and 2) and the incidence surface 13 of the phosphor element 6.

According to FIG. 4, thus increasing the angular extent of the deflected pump light beam 5, an increasing number of phosphor element sections is irradiated, beginning with the central one, e.g. 6b in FIG. 4a) or 6d in FIG. 4c). For irradiating an annular surface of the phosphor element 6 in the present embodiment, a mask can be provided in the path of the pump light beam, for example between the lenses 30 and 31 in FIG. 6.

Figure 7A:
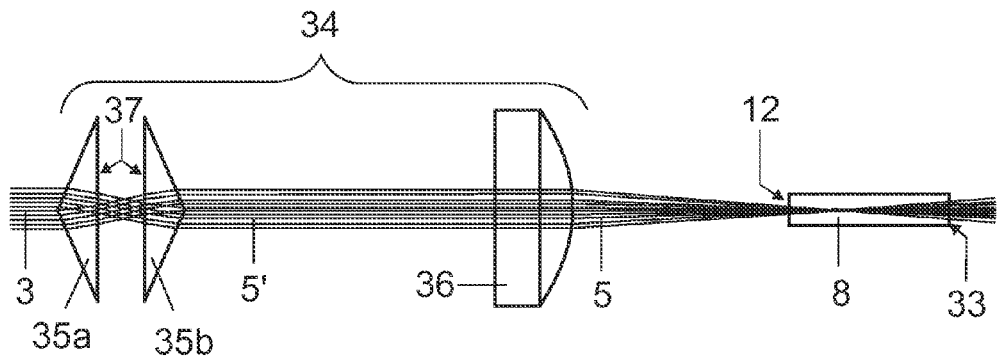
FIGS. 7A-7C show an axicon zoom lens system as an example for a deflecting unit according to the invention.
Figure 7B:
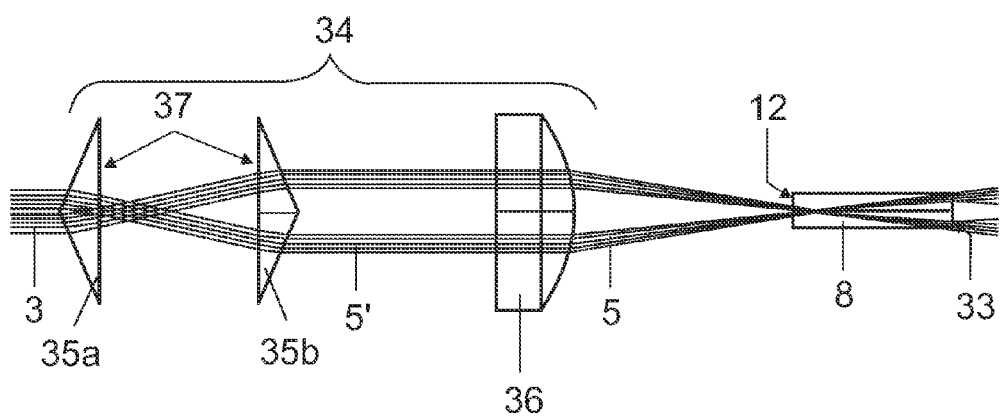
Figure 7C:
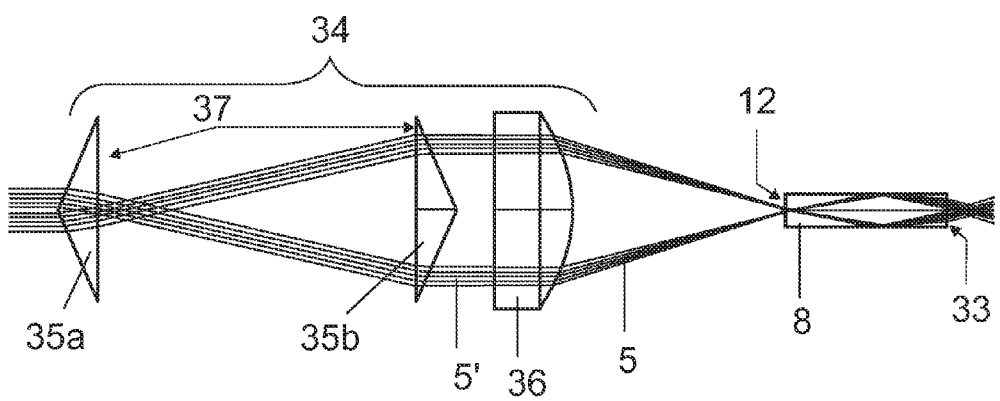

In FIG. 7, an axicon zoom lens system 34 comprising cone shaped lenses 35a/35b, also known as axicons, is employed as a deflecting unit according to the invention. Therein, the initial pump light beam 3, preferably pre-widened in a homogenous manner, having a circular profile shape is centrally incident on the axicon lens 35a along its axis. The axicon 35a imposes an annular angular distribution to the profile of the initial pump light beam 3 by refraction.

In the exemplary configuration shown in FIG. 7, the bases 37 of the two axicon lenses 35a and 35b are facing each other, so that the deflection angle of the pump light beam 5' exiting the axicon lens 35b is zero with respect to the axicon axis at any of the displayed relative positions of the axicons 35a/35, as can be seen in FIG. 7.

For coupling the deflected pump light beam 5', respectively, 5 to the light guide 8, a further positive lens 36 is provided. The angular extent of the deflected pump light beam 5 coupled to the light guide 8 is varied in a manner analogous to that illustrated in FIG. 6, i.e., by moving the axicon lens 35b along the pump light beam 5' with respect to the stationary lenses 35a and 36. As in FIG. 6, the smallest and the largest angular extent is obtained here for the deflected pump light beam 5 by the configurations shown in FIG. 7a) and FIG. 7c), respectively.

In contrast to the zoom lens system 29 shown in FIG. 6, the axicon zoom lens system 34 enables an irradiation of an annular area of a variable lateral extent on a phosphor element provided at the exit side 33 of the light guide 8, such as the phosphor element 6 shown in FIGS. 4a)-4c).

In FIG. 8, a simple implementation of a deflecting unit according to the invention is displayed, comprising a positive lens 38 which is transversely moved with respect to a relatively narrow (not pre-widened in contrast to the FIGS. 6, 7) initial pump light beam 3. As shown in FIG. 8a), the beam 3 is not deflected as a whole if it is incident centrally on the lens 38. In fact, the beam 3 is merely collimated by the lens 38 in this case, the effect being the smaller the thinner the lens 38 is. As the lens axis 39 is gradually moved away from the initial pump light beam 3 in FIGS. 8b)-8d), the deflection of the beam 5 as a whole with respect to the initial direction of propagation of the beam 3 grows. For coupling the deflected beam 5 to a light guide 8 (not shown), a coupling lens system comprising two positive lenses 10 is provided, in analogy to FIGS. 1, 2, 5, and is forming an image of that area on the deflecting lens, which is irradiated by the pump light, on the light guide entry face.

Figure 9:
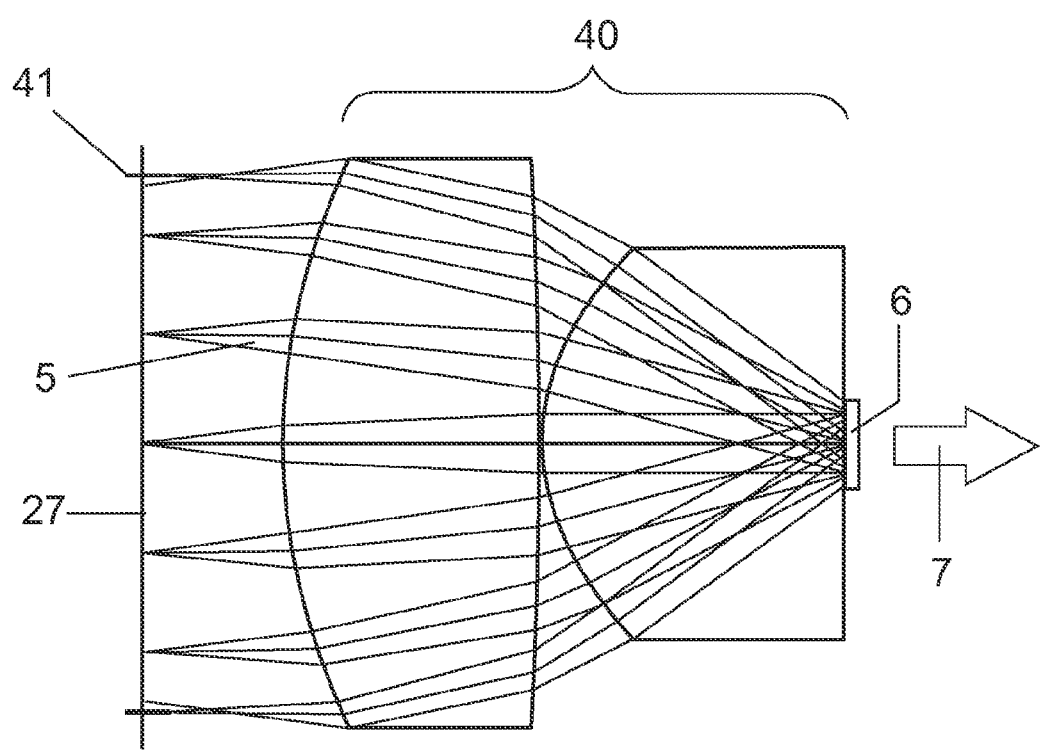
FIG. 9 shows a part of a light source unit according to the invention, wherein the phosphor element is operated in transmission and a focusing lens system focuses the pump light beam to the phosphor element.

In FIG. 9, a focusing lens system 40 is displayed which focuses the pump light beam 5, prepared by means of a deflecting unit according to the invention, for example such as shown in the previous FIGS. 1-3 and 5-8, onto the phosphor element 6 according to the invention, for example such as shown in FIG. 4. Here, the phosphor element 6 is operated in a transmission mode, the converted light 7 intended for further use propagating in a direction indicated by an arrow. As in the embodiment shown in FIG. 3, a dichroic mirror 27 is provided for reflecting the backscattered converted light photons, which is arranged in the entrance pupil 41 of the lens system 40, here.

Figure 10:
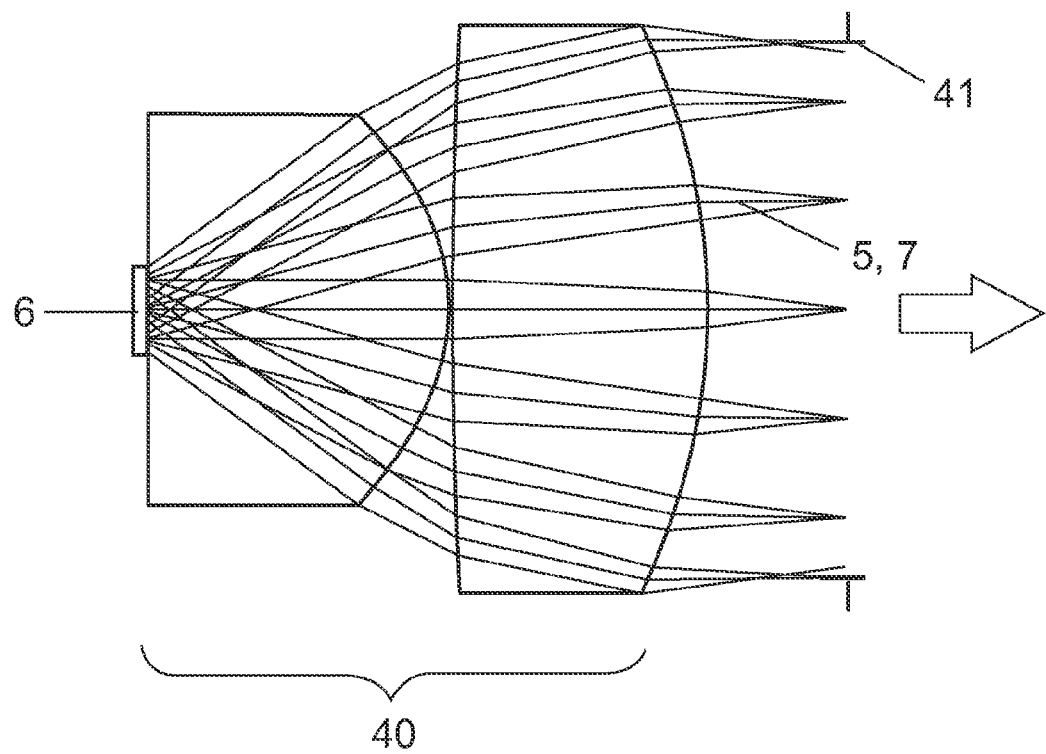
FIG. 10 shows a part of a light source unit according to the invention, wherein the phosphor element is operated in reflection and a lens system is simultaneously used for focusing the pump light and for collecting the converted light.

In contrast thereto, the phosphor element 6 is operated in a reflection mode in FIG. 10. Thus, the focusing lens system 40 focusing the deflected pump light 5 is simultaneously used for collecting the converted light 7 in this embodiment. The entrance pupil 41 can be reasonably used for providing a dichroic mirror 28 for coupling the deflected pump light 5 to the optical system 40, as in the following embodiment illustrated in FIG. 11 or also in a previously described embodiment in FIG. 5.

In FIG. 11, an embodiment of a light source unit 1 according to the invention is displayed, which is suited for an application in a fibre-optical illumination system, for example for medical or industrial endoscopy. Since the phosphor element 6 is operated in a reflection mode, it is provided on the cooling element 14 in analogy to the embodiments described in FIGS. 1 and 2, the present configuration thus being suited for relatively high power levels of the pump light 3, 5.

In the present case of a fibre-optical application, the converted pump light 7 is transmitted to the target 17 to be illuminated by a fibre 42, in general by a light guide similar to the light guide 8 employed for transmitting the pump light in the above-described embodiments. Preferably, the pump light beam 7 is coupled to the fibre 42 by a positive lens system 43.

Figure 12A:
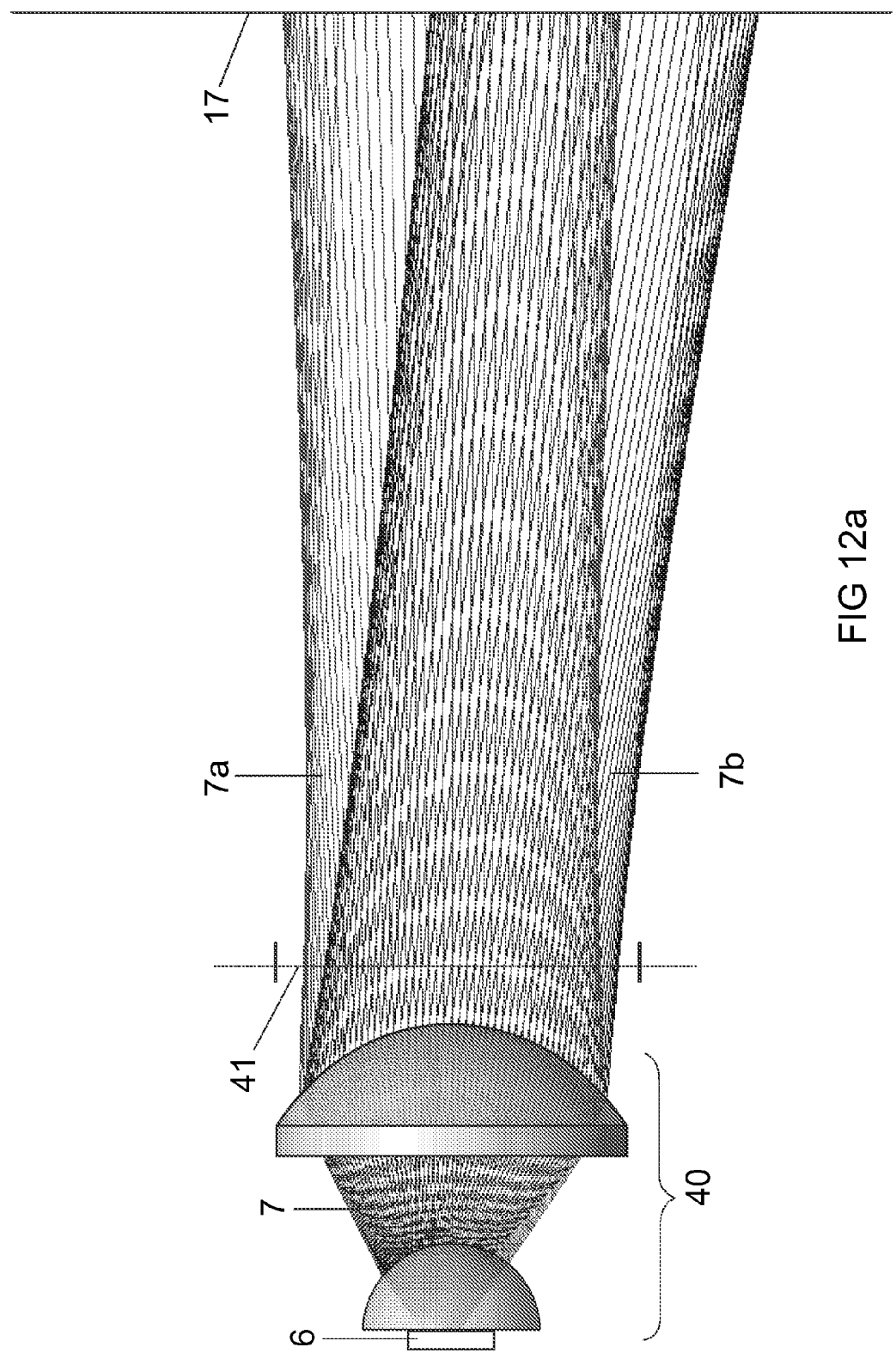
FIG. 12A shows a converted light beam comprising two fractions of the converted light beam emanating from different phosphor element sections, wherein the respective illuminated areas on a distant target screen are shifted with respect to each other.

FIG. 12a) addresses a problem emerging when a distant target 17 needs to be illuminated by the converted light beam 7 in far field, for instance in applications concerning spotlight devices. In the figure, two distinct fractions 7a and 7b of the converted light beam 7 are shown, emanating from two different phosphor element sections of the phosphor element 6. Collimated by the collecting lens system 40, the beams 7a/7b propagate at slightly different angles with respect to each other. As a result, the areas illuminated by the respective beams 7a/7b on the distant target 17 do not completely overlap, so that the respective colours are partially separated. Thus, for those applications of the light source unit in which converted light 7 illuminates the target 17 in far field, an additional optical mixing element needs to be provided in order to obtain the desired homogeneous superposition of converted light emanating from different phosphor element sections.

Figure 12B:
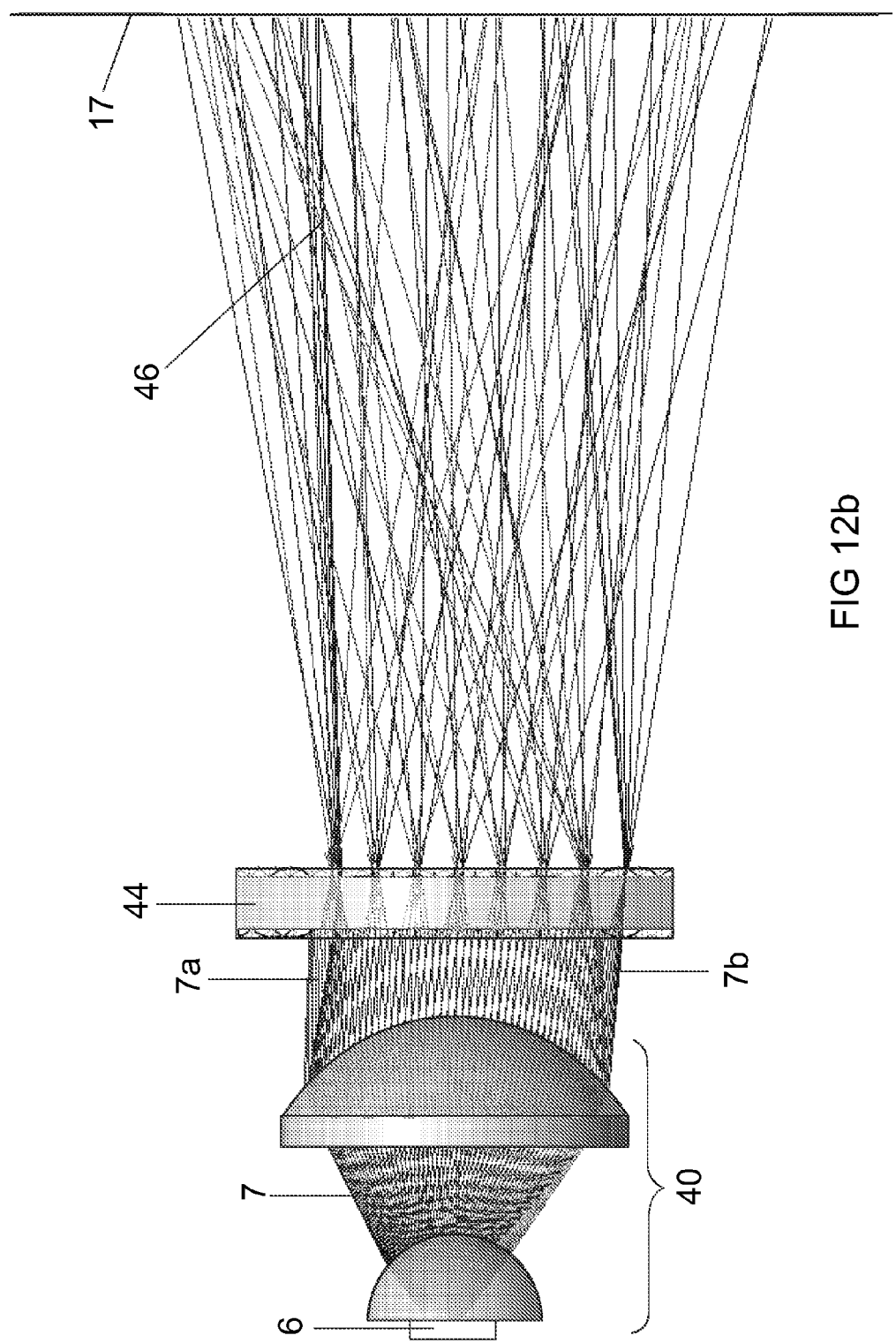
FIG. 12B illustrates a mixing function of a fly's eye condenser provided in the converted light beam shown in FIG. 12A.

In FIG. 12b), a fly's eye condenser 44, described in more detail further above, is provided close to the exit pupil 41 of the lens system 40 as a mixing optical element for obtaining a homogeneous mixture of the respective fractions 7a/7b of the converted light beam 7 emanating from the different phosphor element sections in a combined converted light beam 46 incident on the target 17.

Figure 12C:
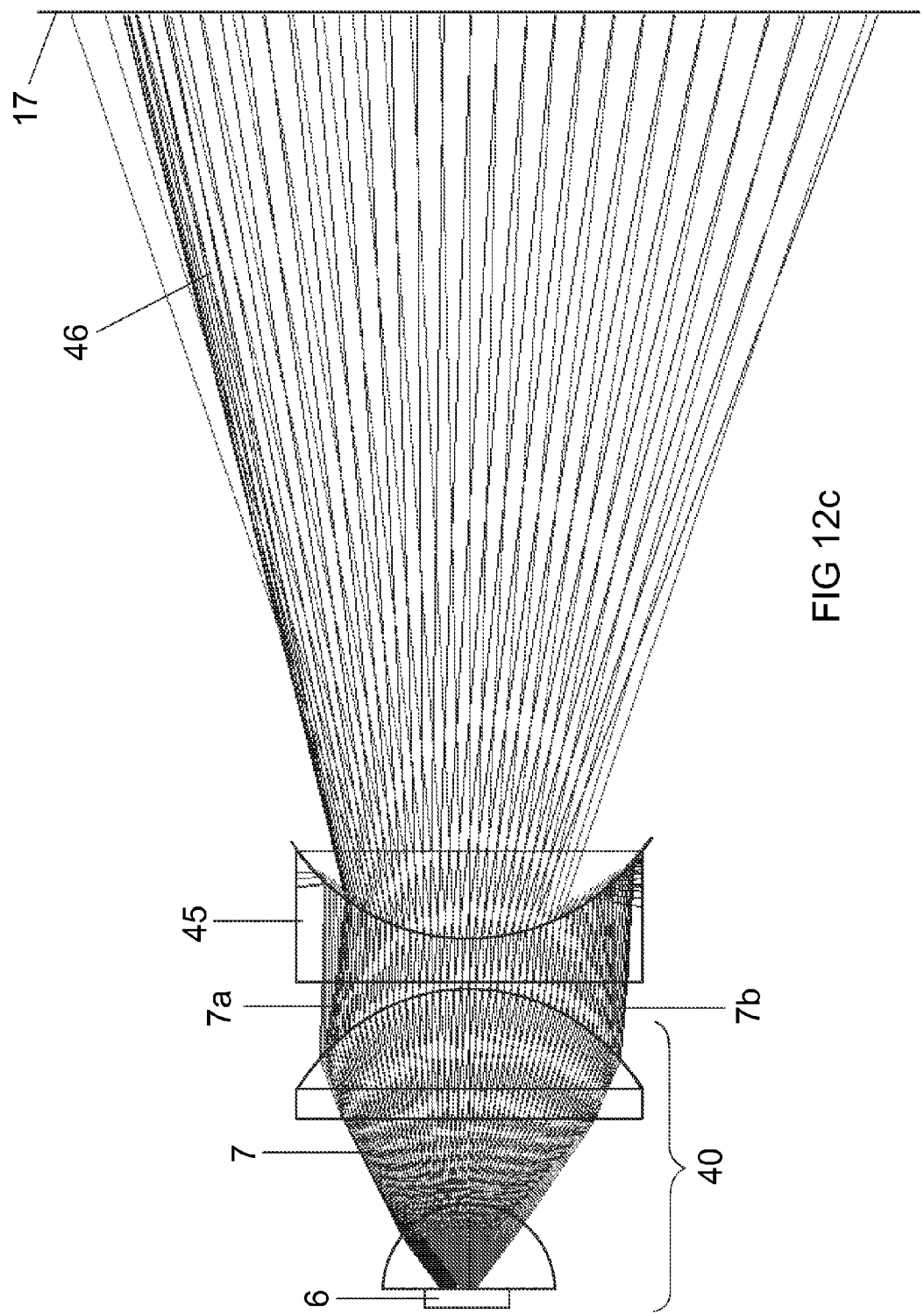
FIG. 12C illustrates a mixing of the respective fractions of the converted light beam as in FIG. 12A obtained by means of an additional lens.

In FIG. 12c), a negative lens system 45 is employed instead of the fly's eye condenser 44 in FIG. 12b) for the same purpose. A combination of negative lenses with masks fading out narrow edge regions of the combined converted light beam 46 is also conceivable for the system 45, as is recognizable from the simulation displayed in the figure.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A light source unit comprising
a pump light source for an emission of pump light,
a phosphor element for a conversion of said pump light into converted light for further use, which phosphor element comprises at least two phosphor element sections interacting differently with said pump light and being suitably arranged for an irradiation in at least one of a simultaneous and a selective manner by said pump light, and
a deflecting unit for deflecting at least a part of said pump light for varying said irradiation by altering a distribution of said pump light incident on said phosphor element with respect to said phosphor element sections in order to vary spectral properties of said converted light,
wherein said deflecting unit comprises a lens system for deflecting at least a part of said pump light intended for incidence onto said phosphor element, wherein said lens system comprises an axicon lens for generating an annular profile shape in a beam of said deflected pump light.

2. The light source unit according to claim 1, wherein said pump light is incident in a main propagation direction onto said phosphor element, and said phosphor element sections are rotationally symmetric with respect to said main propagation direction in a plane perpendicular thereto.

3. The light source unit according to claim 1, wherein said deflecting unit comprises a variable diffraction grating for deflecting at least a part of said pump light intended for incidence onto said phosphor element.

4. The light source unit according to claim 1, wherein said lens system is a zoom lens system for varying a cross-sectional size of a beam of said deflected pump light.

5. The light source unit according to claim 1, wherein said lens system is transversally movable within a beam of said pump light for varying an angle of deflection of said deflected pump light with respect to a main direction of propagation of said pump light entering said deflecting unit.

6. The light source unit according to claim 1, wherein a light guide is provided between said deflecting unit and said phosphor element for transmitting at least a part of said deflected pump light to said phosphor element.

7. The light source unit according to claim 6, wherein a coupling lens system is provided between said deflecting unit and an entry face of said light guide for coupling at least a part of said deflected pump light to said light guide.

8. The light source unit according to claim 6, wherein a focusing lens system is provided between an exit face of said light guide and said phosphor element for focusing said transmitted pump light exiting said light guide towards said phosphor element.

9. The light source unit according to claim 1, wherein a collecting lens system is provided for collecting at least a part of said converted light emanating from said phosphor element, said collecting lens system providing an exit pupil for a beam of said converted light intended for further use.

10. The light source unit according to claim 1, wherein a mixing optical element is provided in a path of said converted light for mixing said converted light emanating from said at least two different phosphor element sections with respect to coordinates in a plane perpendicular to said path for obtaining a beam of said converted light having a uniform cross-sectional distribution of spectral properties at a target to be illuminated.

11. The light source unit according to claim 10, wherein said mixing optical element is arranged in said exit pupil of said collecting lens system.

12. The light source unit according to claim 9, wherein a mirror is provided in said exit pupil of said collecting lens system and at least a part of said pump light is coupled to said mirror for being directed to said phosphor element.

13. The light source unit according to claim 1, wherein a main direction of propagation of said pump light incident on said phosphor element and a main direction of propagation of said converted light at said phosphor element are approximately opposite to each other and said phosphor element is provided on a heat sink not being translucent for said pump light.

14. The light source unit according to claim 1, wherein a main direction of propagation of said pump light incident on said phosphor element and a main direction of propagation of said converted light at said phosphor element approximately coincide and a dichroic mirror is provided in a path of said pump light incident onto said phosphor element, for reflecting at least a part of said converted light emanating from said phosphor element in a direction opposite to either of said main propagation directions.

15. A surgical illumination system for illuminating surgical operating field comprising: a pump light source for an emission of pump light, a phosphor element for a conversion of said pump light into converted light for further use, which phosphor element comprises at least two phosphor element sections interacting differently with said pump light and being suitably arranged for an irradiation in at least one of a simultaneous and a selective manner by said pump light, and a deflecting unit for deflecting at least a part of said pump light for varying said irradiation by altering a distribution of said pump light incident on said phosphor element with respect to said phosphor element sections in order to vary spectral properties of said converted light,
wherein said deflecting unit comprises a lens system for deflecting at least a part of said pump light intended for incidence onto said phosphor element,
wherein said lens system comprises an axicon lens for generating an annular profile shape in a beam of said deflected pump light.

16. A moving head spotlight, comprising: a pump light source for an emission of pump light, a phosphor element for a conversion of said pump light into converted light for further use, which phosphor element comprises at least two phosphor element sections interacting differently with said pump light and being suitably arranged for an irradiation in at least one of a simultaneous and a selective manner by said pump light, and a deflecting unit for deflecting at least a part of said pump light for varying said irradiation by altering a distribution of said pump light incident on said phosphor element with respect to said phosphor element sections in order to vary spectral properties of said converted light,
  wherein said deflecting unit comprises a lens system for deflecting at least a part of said pump light intended for incidence onto said phosphor element,
  wherein said lens system comprises an axicon lens for generating an annular profile shape in a beam of said deflected pump light.

17. A projection system, comprising: a pump light source for an emission of pump light, a phosphor element for a conversion of said pump light into converted light for further use, which phosphor element comprises at least two phosphor element sections interacting differently with said pump light and being suitably arranged for an irradiation in at least one of a simultaneous and a selective manner by said pump light, and a deflecting unit for deflecting at least a part of said pump light for varying said irradiation by altering a distribution of said pump light incident on said phosphor element with respect to said phosphor element sections in order to vary spectral properties of said converted light,
  wherein said deflecting unit comprises a lens system for deflecting at least a part of said pump light intended for incidence onto said phosphor element,
  wherein said lens system comprises an axicon lens for generating an annular profile shape in a beam of said deflected pump light.

18. A fibre-optical illumination system, comprising: a pump light source for an emission of pump light, a phosphor element for a conversion of said pump light into converted light for further use, which phosphor element comprises at least two phosphor element sections interacting differently with said pump light and being suitably arranged for an irradiation in at least one of a simultaneous and a selective manner by said pump light, and a deflecting unit for deflecting at least a part of said pump light for varying said irradiation by altering a distribution of said pump light incident on said phosphor element with respect to said phosphor element sections in order to vary spectral properties of said converted light,
  wherein said deflecting unit comprises a lens system for deflecting at least a part of said pump light intended for incidence onto said phosphor element,
  wherein said lens system comprises an axicon lens for generating an annular profile shape in a beam of said deflected pump light.

19. A method for varying spectral properties of light emanating from a light source unit comprising a pump light source for an emission of pump light, a phosphor element for a conversion of said pump light into converted light for further use, which phosphor element comprises at least two phosphor element sections interacting differently with said pump light and being suitably arranged for an irradiation in at least one of a simultaneous and a selective manner by said pump light, and a deflecting unit for deflecting at least a part of said pump light for varying said irradiation, also in combination with one of claims 2 to 14, the method comprising a step of adjusting said deflecting unit for altering a distribution of said pump light incident on said phosphor element with respect to said phosphor element sections for varying spectral properties of said converted light,
  wherein said deflecting unit comprises a lens system for deflecting at least a part of said pump light intended for incidence onto said phosphor element,
  wherein said lens system comprises an axicon lens for generating an annular profile shape in a beam of said deflected pump light.

20. The light source unit according to claim 1, said lens system further comprising a second axicon lens, wherein the bases of the axicon lens and the second axicon lens are facing each other such that the deflection angle of said pump light exiting the second axicon lens is zero with respect to the axicon axis at any of the displayed relative positions of the axicons.

* * * * *